US00PP13980P29

(12) United States Plant Patent
Hanes

(10) Patent No.: US PP13,980 P2
(45) Date of Patent: Jul. 15, 2003

(54) VERBENA PLANT NAMED 'LAN ROY PUR'

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/057,987

(22) Filed: Jan. 29, 2002

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Annette H. Para
(74) *Attorney, Agent, or Firm*—Jondle & Associates PC

(57) ABSTRACT

A verbena cultivar particularly distinguished by purple colored flowers, vigorous growth and semi-trailing habit.

1 Drawing Sheet

GENUS AND SPECIES

Verbena hybrida.

VARIETY DENOMINATION

'Lan Roy Pur'.

BACKGROUND OF THE NEW PLANT

The present invention comprises a new and distinct cultivar of verbena, botanically known as Verbena hybrida, and hereinafter referred to by the cultivar name 'Lan Roy Pur'. The new cultivar is asexually reproduced from vegetative cuttings and tissue culture resulting from the cross of the seed/pod parent 98-697-2, an unnamed and unpatented rose-purple proprietary line and the pollen parent Temari Purple (PPAF), a commercial line.

'Lan Roy Pur' is a product of a planned breeding program intended to create new verbena cultivars with purple colored flowers, dark green foliage, vigorous growth and semi-trailing habit.

The new cultivar was created in 1999 in Gilroy, Calif. and has been asexually reproduced repeatedly by vegetative cuttings and tissue culture in Gilroy, Calif. over a two year period. It has also been trialed at Gilroy, Calif.; Alberta, Canada, Mich. Litchfield, Mich. and Andijk, The Netherlands. The present invention has been found to retain its distinctive characteristics through successive propagations; and this novelty is firmly fixed.

DESCRIPTION OF PHOTOGRAPH

This new verbena plant is illustrated by the accompanying photograph which shows blooms, buds, and foliage of the plant in full color, the colors shown being as true as can be reasonably obtained by conventional photographic procedures.

The drawing shows overall plant habit; and the mature inflorescence.

DESCRIPTION OF THE NEW CULTIVAR

The following detailed descriptions set forth the distinctive characteristics of 'Lan Roy Pur'. The data which defines these characteristics were collected from asexual reproductions carried out in Alberta Canada. The plant history was taken on 11 week old plants grown in 4 inch pots, blossomed under natural light in a greenhouse and color readings were taken in the greenhouse in Alberta Canada. Color references are primarily to The R.H.S. Colour Chart of The Royal Horticultural Society of London (R.H.S.).

THE PLANT

Classification:
*Botanical.*—Verbena hybrida.
*Commercial.*—Verbena.
Form: Low trailing annual, decumbent.
Growth and branching habit: Vigorous growing, moderate basal branching; low trailing habit.
Height: From soil level to top of blooms: Approximately 9 cm.
Width: Approximately 59 cm.
Time to produce a finished flowering plant: 11 weeks.
Outdoor plant performance: Typical bedding plant culture, full sun in the garden, hanging baskets or container plants.
Time to initiate roots: Approximately 4 days in the greenhouse.
Time to develop roots: Approximately 7 days in the greenhouse.
Root description: Fibrous, fleshy, white.

THE LEAVES

Length: 3.4–4.8 cm.
Width: 2.1–3.2 cm.
Leaf blade shape: Ovate lanceolate.
Leaf margin: Irregular, crenately incised.
Apex aspect: Obtuse.
Base aspect: Cuneate or truncate.
Foliage color: Upper surface — Yellow-green RHS 147A; Lower surface is yellow-green RHS 147B.
Texture: Moderately hairy.
Venation: Pinnatifid, pubescent.
Venation color: Upper surface is yellow-green RHS 147C; lower surface is yellow-green RHS 147C.
Petiole length: 8 mm.
Petiole diameter: 2 mm.
Petiole color: Upper surface is yellow-green RHS 147C; lower surface is yellow-green RHS 145A.

THE STEM

Length: 15–29 cm.
Diameter: 3.0 mm.
Internode length: 2.5–3.3 cm.
Color: Upper surface is yellow-green RHS 146A; lower surface is yellow-green RHS 144A.
Texture: Moderately hairy.
Anthocyanin: Weak anthocyanin on stem, with stronger intensity along stem edge.

THE BUD

Shape: Linear.
Diameter: 2–3 mm.
Length: 15 mm.
Color at tight bud: Purple RHS 77A with dark purple RHS 83A on margin edge.

THE FLOWER

Blooming habit: Continuous throughout the growing season.
Inflorescence type: Spike.
Spikes per plant: 19–32.
Spike diameter: Approximately 6.0 cm.
Spike depth: Approximately 3.4 cm.
Peduncle length: 4.0–7.7 cm.
Peduncle diameter: 2 mm.
Peduncle color: Yellow-green RHS 146A.
Peduncle texture: Very pubescent.
Flower color: Upper petal surface is purple RHS 77A with secondary color towards center of purple RHS N79C; Lower petal surface is purple RHS 77B.
Floret form: Salverform; sessile on spikes.
Floret (limb) diameter: Approximately 23.5 mm.
Corolla tube length: Approximately 19 mm.
Number florets per spike: 18–24 (closed to fully open florets).
Number of petals: Gamopetalous, five lobed.
Petal size:
*Length of one lobe.*—10 mm.
*Width of one lobe.*—1.1 cm.
Petal lobe shape: Obcordate.
Petal apex shape: Deeply emarginate.
Petal base shape: Fused.
Petal margin: Entire.
Petal texture: Smooth with fine pubescence.
Sepals: Five sepals whose margins are fused to each other along their length with a transparent membrane of less than 1 mm in width with one smaller sepal (3 mm) attached to the base of the calyx.
Calyx length: Approximately 14 mm.
Calyx width: Approximately 5 mm.
Calyx shape: Linear.
Calyx apex: Acute.
Calyx color: Yellow-green RHS 137C.
Lastingness of individual blooms: One week.
Fragrance: None.

THE REPRODUCTIVE ORGANS

Stamens: Anthers and filaments fused to upper half of corolla tube; four anthers with two pollen sacs per anther.
Pollen amount and color: Moderate, yellow RHS 1A.
Pistil: One style approximately 18 mm; transparent to yellow RHS 1D throughout length with yellow-green RHS 144C and short stripes of greyed orange RHS 176C near tip, slightly curved at the tip with one stigma yellow-green RHS 144A.
Fruit seed set: Does not freely set seed but can produce 4 narrow nutlets, approximately 4 mm long; colored grey-brown RHS 199D and enclosed in the dried calyx.

DISEASE AND INSECT RESISTANCE

Tolerant to mildew

COMPARISON WITH KNOWN CULTIVARS

When the instant plant is compared to 'Temari Violet' (PPAF) the 'Lan Roy Pur' stem color is darker than 'Temari Violet'. 'Lan Roy Pur' has leaves that are narrower and the pubescence on the upper surface is less than 'Temari Violet'. Additionally, the flower density of 'Lan Roy Pur' is greater than that of 'Temari Violet'.

COMPARISON WITH PARENTAL CULTIVARS

When comparing 'Lan Roy Pur' to the female parent, 98-697-2, 'Lan Roy Pur' has an upright trailing habit while 98-697-2 has more upright habit and is less trailing. 'Lan Roy Pur' has a deep purple color while 98-697-2 has a rose purple flower color. 'Lan Roy Pur' is more mildew tolerant than 98-697-2. When comparing 'Lan Roy Pur' to the male parent, 'Temari Purple', 'Lan Roy Pur' has a deep purple color while 'Temari Purple' has a slightly lighter purple color. 'Land Roy Pur' is basal branching with a slightly upright plant habit while 'Temari Purple' is less basal branching and has a flat habit.

I claim:

1. A new and distinct plant of verbena as shown and described herein.

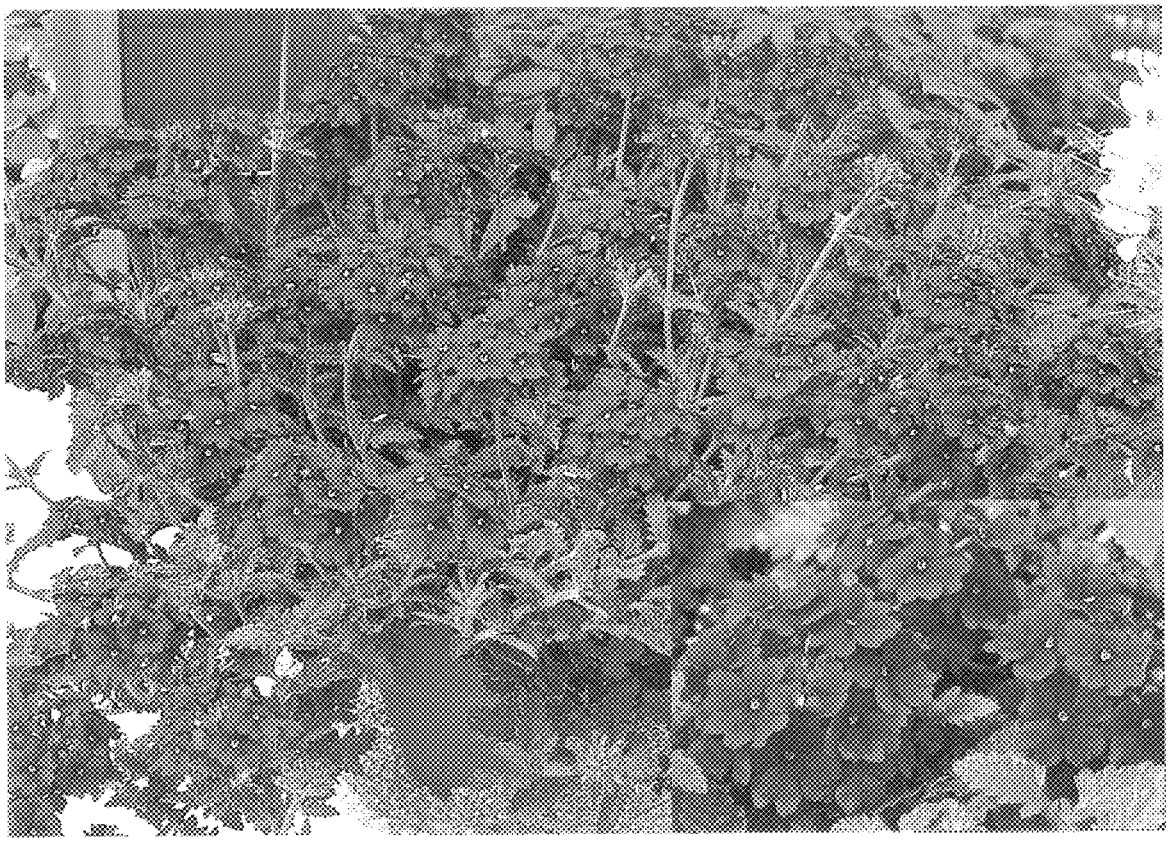

* * * * *